(12) United States Patent
Iczkiewicz et al.

(10) Patent No.: US 7,790,687 B2
(45) Date of Patent: Sep. 7, 2010

(54) TREATMENT FOR NEURODEGENERATION

(75) Inventors: Joanna Iczkiewicz, London (GB); Peter Jenner, London (GB)

(73) Assignee: Proximagen Ltd., London (GB)

( * ) Notice: Subject to any disclaimer, the term of this patent is extended or adjusted under 35 U.S.C. 154(b) by 286 days.

(21) Appl. No.: 11/884,279

(22) PCT Filed: Feb. 17, 2006

(86) PCT No.: PCT/GB2006/000589

§ 371 (c)(1),
(2), (4) Date: Aug. 14, 2007

(87) PCT Pub. No.: WO2006/087579

PCT Pub. Date: Aug. 24, 2006

(65) Prior Publication Data

US 2009/0137463 A1   May 28, 2009

Related U.S. Application Data

(60) Provisional application No. 60/653,960, filed on Feb. 18, 2005.

(51) Int. Cl.
*A61K 38/00* (2006.01)
*A61K 39/00* (2006.01)
*A61K 39/38* (2006.01)
*A01N 37/18* (2006.01)

(52) U.S. Cl. .................. 514/14; 424/184.1; 424/185.1; 424/198.1; 514/2

(58) Field of Classification Search ........................ None
See application file for complete search history.

(56) References Cited

U.S. PATENT DOCUMENTS 7,217,687 B2 *   5/2007   Boschert et al. ................ 514/2

FOREIGN PATENT DOCUMENTS

WO   WO 02/092122   11/2002

OTHER PUBLICATIONS

Welsh, 1999, Current Opinion in Mol. Therapeutics, 1 (4), pp. 464-470.*
Iczkiewicz Joanna et al., "Increased Osteopontin Expression Following Intranigral Lipopolysaccharide Injection in the rat." The European Journal of Neuroscience. Apr. 2005 vol. 21, No. 7, pp. 1911-1920, XP002377373.
Iczkiewicz et al., "Osteopontin (Eta-1) is present in the rat basal ganglia" Molecular Brain Research, Elsevier Science BV, Amsterdam, NL, vol. 132, No. 1, Dec. 6, 2004 pp. 64-72, XP004645597.
Iczkiewicz et al., "Osteopontin and Tyrosine Hydroxylase Expression Following Intranigral Injection of Lipopolysaccharide." British Journal of Pharmacology, vol. 138, No. Proceedings Supplement, Apr. 2003. p. 201P, XP009065492 & Proceedings oof the British Pharmacological Society Meeting; Brighton, UK; Jan. 8-10, 2003.

* cited by examiner

*Primary Examiner*—Olga N Chernyshev
(74) *Attorney, Agent, or Firm*—Banner & Witcoff, Ltd.

(57) ABSTRACT

Polypeptides which are an N- and/or C-terminally truncated fragment of the human osteopontin (hOPN) sequence or species variant, and which minimally have a 15 amino acid sequence corresponding to amino acids 138 to 152 of hOPN, and polynucleotides encoding said polypeptide, are useful for treatment or prevention of neurodegeneration.

5 Claims, 9 Drawing Sheets a b c

SEQUENCE LISTING

```
<160> NUMBER OF SEQ ID NOS: 13

<210> SEQ ID NO 1
<211> LENGTH: 1447
<212> TYPE: DNA
<213> ORGANISM: Homo sapiens

<400> SEQUENCE: 1
gaggcagcag cagcaggagg aggcagacac agcatcgtcg ggaccagact cgtctcaggc      60
cagttgcagc cttctcagcc aaacgccgac caaggaaaac tcactaccat gagaattgca     120
gtgatttgct tttgcctcct aggcatcacc tgtgccatac cagttaaaca ggctgattct     180
ggaagttctg aggaaaagca gctttacaac aaatacccag atgctgtggc cacatggcta     240
aaccctgacc catctcagaa gcagaatctc ctagcccac agacccttcc aagtaagtcc     300
aacgaaagcc atgaccacat ggatgatatg gatgatgaag atgatgatga ccatgtggac     360
agccaggact ccattgactc gaacgactct gatgatgtag atgacactga tgattctcac     420
cagtctgatg agtctcacca ttctgatgaa tctgatgaac tggtcactga ttttcccacg     480
```

-continued

```
gacctgccag caaccgaagt tttcactcca gttgtcccca cagtagacac atatgatggc      540
cgaggtgata gtgtggttta tggactgagg tcaaaatcta agaagtttcg cagacctgac      600
atccagtacc ctgatgctac agacgaggac atcacctcac acatggaaag cgaggagttg      660
aatggtgcat acaaggccat ccccgttgcc caggacctga acgcgccttc tgattgggac      720
agccgtggga aggacagtta tgaaacgagt cagctggatg accagagtgc tgaaacccac      780
agccacaagc agtccagatt atataagcgg aaagccaatg atgagagcaa tgagcattcc      840
gatgtgattg atagtcagga actttccaaa gtcagccgtg aattccacag ccatgaattt      900
cacagccatg aagatatgct ggttgtagac cccaaaagta aggaagaaga taaacacctg      960
aaatttcgta tttctcatga attagatagt gcatcttctg aggtcaatta aaaggagaaa     1020
aaatacaatt tctcactttg catttagtca aagaaaaaa tgctttatag caaaatgaaa     1080
gagaacatga aatgcttctt tctcagttta ttggttgaat gtgtatctat ttgagtctgg     1140
aaataactaa tgtgtttgat aattagttta gtttgtggct tcatggaaac tccctgtaaa     1200
ctaaaagctt cagggttatg tctatgttca ttctatagaa gaaatgcaaa ctatcactgt     1260
attttaatat ttgttattct ctcatgaata gaaatttatg tagaagcaaa caaaatactt     1320
ttacccactt aaaaagagaa tataacattt tatgtcacta taatctttg tttttaagt      1380 tagtgtatat tttgttgtga ttatctttt gtggtgtgaa taaatctttt atcttgaatg     1440
taataag                                                                 1447
```

```
<210> SEQ ID NO 2
<211> LENGTH: 300
<212> TYPE: PRT
<213> ORGANISM: Homo sapiens
<220> FEATURE:
<221> NAME/KEY: PHOSPHORYLATION
<222> LOCATION: (24)..(30)
<223> OTHER INFORMATION: Caesin kinase II phosphorylation sites
<220> FEATURE:
<221> NAME/KEY: CA_BIND
<222> LOCATION: (72)..(81)
<220> FEATURE:
<221> NAME/KEY: SITE
<222> LOCATION: (143)..(155)
<223> OTHER INFORMATION: Cell adhesion domain (integriin binding site)
<220> FEATURE:
<221> NAME/KEY: SITE
<222> LOCATION: (154)..(155)
<223> OTHER INFORMATION: Thrombin cleavage site
<220> FEATURE:
<221> NAME/KEY: CA_BIND
<222> LOCATION: (202)..(213)
<220> FEATURE:
<221> NAME/KEY: SITE
<222> LOCATION: (277)..(300)
<223> OTHER INFORMATION: Heparin binding site

<400> SEQUENCE: 2

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Asp Glu Asp Asp Asp
65                  70                  75                  80
```

```
Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 3
<211> LENGTH: 154
<212> TYPE: PRT
<213> ORGANISM: Homo sapiens

<400> SEQUENCE: 3

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Thr Leu Pro Ser Lys Ser
        50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg
145                 150
```

<210> SEQ ID NO 4
<211> LENGTH: 15
<212> TYPE: PRT
<213> ORGANISM: Homo sapiens

<400> SEQUENCE: 4

Thr Val Asp Thr Tyr Asp Gly Arg Gly Asp Ser Val Val Tyr Gly
1               5                   10                  15

<210> SEQ ID NO 5
<211> LENGTH: 1457
<212> TYPE: DNA
<213> ORGANISM: Rattus norvegicus

<400> SEQUENCE: 5

```
gcaagcctca gcatccttgg ctttgcagtc tcctgcggca agcattctcg aggaagccag      60
ccaaggacca actacaacca tgagactggc agtggtttgc ctttgcctgt tcggccttgc     120
ctcctgtctc ccggtgaaag tggctgagtt tggcagctca gaggagaagg cgcattacag     180
caaacactca gatgctgtag ccacttggct gaagcctgac ccatctcaga agcagaatct     240
tctagcccca cagaattctg tgtcctctga gaaacggat gactttaagc aagaaactct      300
tccaagcaac tccaatgaaa gccatgacca catggacgat gatgacgacg acgatgacga     360
cggagaccat gcagagagcg aggattctgt gaactcggat gaatctgacg aatctcacca     420
ttccgatgaa tctgatgagt ccttcactgc cagcacacaa gcagacgttt tgactccaat     480
cgcccccaca gtcgatgtcc ctgacggccg aggtgatagc ttggcttacg gactgaggtc     540
aaagtccagg agtttccctg tttctgatga acagtatccc gatgccacag atgaggacct     600
cacctcccgc atgaagagcc aggagtccga tgaggctatc aaggtcatcc cagttgccca     660
gcgtctgagc gtgccctctg atcaggacag caacgggaag accagccatg agtcaagtca     720
gctggatgaa ccaagcgtgg aaacacacag cctggagcag tccaaggagt ataagcagag     780
ggccagccac gagagcactg agcagtcgga tgcgatcgat agtgccgaga agccggatgc     840
aatcgatagt gcagagcggt cggatgctat cgacagtcag gcgagttcca aagccagcct     900
ggaacatcag agccacgagt tcacagccat gaggacaag ctagtcctag accctaagag      960
taaggaagat gataggtatc tgaaattccg catttctcat gaattagaga gttcatcttc    1020
tgaggtcaat taagaagag gcaaaaccac agttccttac tttgctttaa ataaaacaaa    1080
aagtaaattc caacaagcag gaatactaac tgcttgtttc tcagttcagt ggatacatgt    1140
atgtggagaa agaaatagat agtgttttgg gccctgagct tagttcgttg tttcatgcag    1200
acaccactgt aacctagaag tttcagcatt tcgcttctgt tctttctgtg caagaaatgc    1260
aaatggccac tgcatttaa tgattgctat tcttttatga ataaaatgta tgtagaggca    1320
ggcaaactta caggaacagc aaaattaaaa gagaaactat aatagtctgt gtcactataa    1380
tcttttggtt ttataattag tgtatatttt gttgtgatta ttttgttgg tgtgaataaa    1440
tcttgtatct tgaatgt                                                  1457
```

<210> SEQ ID NO 6
<211> LENGTH: 317
<212> TYPE: PRT
<213> ORGANISM: Rattus norvegicus

<400> SEQUENCE: 6

Met Arg Leu Ala Val Val Cys Leu Cys Leu Phe Gly Leu Ala Ser Cys

-continued

```
1               5                   10                  15

Leu Pro Val Lys Val Ala Glu Phe Gly Ser Ser Glu Glu Lys Ala His
                20                  25                  30

Tyr Ser Lys His Ser Asp Ala Val Ala Thr Trp Leu Lys Pro Asp Pro
                35                  40                  45

Ser Gln Lys Gln Asn Leu Leu Ala Pro Gln Asn Ser Val Ser Ser Glu
            50                  55                  60

Glu Thr Asp Asp Phe Lys Gln Glu Thr Leu Pro Ser Asn Ser Asn Glu
65                  70                  75                  80

Ser His Asp His Met Asp Asp Asp Asp Asp Asp Asp Asp Asp Gly Asp
                85                  90                  95

His Ala Glu Ser Glu Asp Ser Val Asn Ser Asp Glu Ser Asp Glu Ser
                100                 105                 110

His His Ser Asp Glu Ser Asp Glu Ser Phe Thr Ala Ser Thr Gln Ala
                115                 120                 125

Asp Val Leu Thr Pro Ile Ala Pro Thr Val Asp Val Pro Asp Gly Arg
                130                 135                 140

Gly Asp Ser Leu Ala Tyr Gly Leu Arg Ser Lys Ser Arg Ser Phe Pro
145                 150                 155                 160

Val Ser Asp Glu Gln Tyr Pro Asp Ala Thr Asp Glu Asp Leu Thr Ser
                165                 170                 175

Arg Met Lys Ser Gln Glu Ser Asp Glu Ala Ile Lys Val Ile Pro Val
                180                 185                 190

Ala Gln Arg Leu Ser Val Pro Ser Asp Gln Asp Ser Asn Gly Lys Thr
                195                 200                 205

Ser His Glu Ser Ser Gln Leu Asp Glu Pro Ser Val Glu Thr His Ser
                210                 215                 220

Leu Glu Gln Ser Lys Glu Tyr Lys Gln Arg Ala Ser His Glu Ser Thr
225                 230                 235                 240

Glu Gln Ser Asp Ala Ile Asp Ser Ala Glu Lys Pro Asp Ala Ile Asp
                245                 250                 255

Ser Ala Glu Arg Ser Asp Ala Ile Asp Ser Gln Ala Ser Ser Lys Ala
                260                 265                 270

Ser Leu Glu His Gln Ser His Glu Phe His Ser His Glu Asp Lys Leu
                275                 280                 285

Val Leu Asp Pro Lys Ser Lys Glu Asp Asp Arg Tyr Leu Lys Phe Arg
                290                 295                 300

Ile Ser His Glu Leu Glu Ser Ser Ser Glu Val Asn
305                 310                 315

<210> SEQ ID NO 7
<211> LENGTH: 153
<212> TYPE: PRT
<213> ORGANISM: Rattus norvegicus

<400> SEQUENCE: 7

Met Arg Leu Ala Val Val Cys Phe Cys Leu Phe Gly Leu Ala Ser Cys
1               5                   10                  15

Leu Pro Val Lys Val Ala Glu Phe Gly Ser Ser Glu Glu Lys Ala His
                20                  25                  30

Tyr Ser Lys His Ser Asp Ala Val Ala Thr Trp Leu Lys Pro Asp Pro
                35                  40                  45

Ser Gln Lys Gln Asn Leu Leu Ala Pro Gln Asn Ser Val Ser Ser Glu
            50                  55                  60
```

```
Glu Thr Asp Asp Phe Lys Gln Glu Thr Leu Pro Ser Asn Ser Asn Glu
 65                  70                  75                  80

Ser His Asp His Met Asp Asp Asp Asp Asp Asp Asp Asp Asp Gly Asp
                 85                  90                  95

His Ala Glu Ser Glu Asp Ser Val Asn Ser Asp Glu Ser Asp Glu Ser
            100                 105                 110

His His Ser Asp Glu Ser Asp Glu Ser Phe Thr Ala Ser Thr Gln Ala
        115                 120                 125

Asp Val Leu Thr Pro Ile Ala Pro Thr Val Asp Val Pro Asp Gly Arg
    130                 135                 140

Gly Asp Ser Leu Ala Tyr Gly Leu Arg
145                 150

<210> SEQ ID NO 8
<211> LENGTH: 15
<212> TYPE: PRT
<213> ORGANISM: Rattus norvegicus

<400> SEQUENCE: 8

Thr Val Asp Val Pro Asp Gly Arg Gly Asp Ser Leu Ala Tyr Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: human-rat consensus sequence
<220> FEATURE:
<221> NAME/KEY: misc_feature
<222> LOCATION: (4)..(4)
<223> OTHER INFORMATION: Xaa = Thr or Val
<220> FEATURE:
<221> NAME/KEY: misc_feature
<222> LOCATION: (5)..(5)
<223> OTHER INFORMATION: Xaa = Tyr or Pro
<220> FEATURE:
<221> NAME/KEY: misc_feature
<222> LOCATION: (12)..(12)
<223> OTHER INFORMATION: Xaa = Leu or Val
<220> FEATURE:
<221> NAME/KEY: misc_feature
<222> LOCATION: (13)..(13)
<223> OTHER INFORMATION: Xaa = Val or Ala

<400> SEQUENCE: 9

Thr Val Asp Xaa Xaa Asp Gly Arg Gly Asp Ser Xaa Xaa Tyr Gly
1               5                   10                  15

<210> SEQ ID NO 10
<211> LENGTH: 40
<212> TYPE: DNA
<213> ORGANISM: Rattus norvegicus

<400> SEQUENCE: 10
gatgtcgtag actcacaaag cacattacgc ggaagaggag                           40

<210> SEQ ID NO 11
<211> LENGTH: 40
<212> TYPE: DNA
<213> ORGANISM: Rattus norvegicus

<400> SEQUENCE: 11 acaccccgc taacctcagt tttgcagacg aacacacgac                            40
```

```
<210> SEQ ID NO 12
<211> LENGTH: 40
<212> TYPE: DNA
<213> ORGANISM: rattus norvegicus

<400> SEQUENCE: 12
gatcctgatc gaacaggagt accgacactt tgagcaggca                              40

<210> SEQ ID NO 13
<211> LENGTH: 40
<212> TYPE: DNA
<213> ORGANISM: Rattus norvegicus

<400> SEQUENCE: 13
gcgcctccac tccaggagta gacaccgtag ccctatgaca                              40
```

TREATMENT FOR NEURODEGENERATION

CROSS REFERENCE TO RELATED APPLICATIONS:

This application is a National Stage application of co-pending PCT application PCT/GB2006/000589 filed Feb. 17, 2006, which claims the benefit of U.S. provisional application No. 60/653,960 filed Feb. 18, 2005. These applications are incorporated herein by reference in their entireties.

This application incorporates by reference the contents of a 13.9 KB text file labeled "006029_00029_sequence_listing" and created Mar. 24, 2008, which is the sequence listing for this application.

FIELD OF THE INVENTION

The present invention relates to a method for treating or preventing a neurodegeneration disorder. The method of the invention has particular application in the treatment of Parkinson's disease and other disorders associated with loss of dopaminergic neurons.

BACKGROUND TO THE INVENTION

Parkinson's disease (PD) is one of the most common age-related neurodegenerative disorders. PD is characterised by the selective loss of dopaminergic neurones in the substantia nigra (SN), and the loss of dopamine in the striatum accompanied by the presence of Lewy bodies. Nigral neurodegeneration is also a feature of diseases termed 'Parkinson-plus syndromes' such as multiple system atrophy (MSA) and progressive supranuclear palsy (PSP). The main symptoms of iPD are tremor, rigidity of the limbs and trunk, akinesia, bradykinesia and postural abnormalities, and the severity of these symptoms differs amongst individuals. The initiating cause of PD still remains unknown and therefore investigations into other elements that can initiate neurodegeneration in the SN are being looked into.

Osteopontin (OPN) has been shown to play an important function in oxidative and nitrative stress, in inflammatory processes, in apoptotic pathways as well as possessing calcium binding properties. OPN is a secreted glycosylated phosphoprotein. The size of the secreted protein varies between 44-75 kDa and this is due to differences in post-translational modifications. Variations in glycosylation, phosphorylation, sulphation and thrombin cleavage lead to the generation of differing functional forms of OPN.

The two main receptor types that OPN binds to are the integrin receptors and the CD44 receptors. The integrin receptors are heterodimeric transmembrane proteins formed by non-covalent binding of $\alpha$ and $\beta$ subunits. OPN binds to integrin receptors in either an RGD-dependent or RGD-independent manner. The following integrins bind to the RGD binding motif in OPN: $\alpha_5\beta_1$, $\alpha_8\beta_1$, $\alpha_v\beta_1$, $\alpha_v\beta_3$ and $\alpha_v\beta_5$. The RGD-independent integrins are the $\alpha_4\beta_1$ receptor and the $\alpha_9\beta_1$ receptor which bind via the SVVYGLR sequence, although these receptors only recognise the thrombin cleaved fragment of OPN and not the full length protein. OPN appears to have the highest affinity for the $\alpha_v\beta_3$ receptor.

OPN is constitutively expressed in bone, kidney, brain and blood. In response to a variety of stimuli such as oxidative stress, heat shock and inflammation, OPN can be induced in a wide variety of cells including, epithelial cells, smooth muscle cells, fibroblasts, macrophages, T-lymphocytes and microglial cells. OPN is a multifunctional protein with new functions continuously being discovered. This is due to the existence of numerous, functionally distinct forms, that can differ at the transcriptional level as well as at the post-transitional modification level. In addition, its functions differ according to whether it is present as an immobilised cell adhesion protein or as a soluble protein. OPN is known to regulate cell death, cell survival, migration and tissue remodelling. Elevated OPN expression has been found in a variety of diseases including multiple sclerosis (MS), atherosclerosis, myocardial injury, tuberculosis, osteoarthritis, rheumatoid arthritis and various cancers.

To date there have been no studies on the relationship between OPN and neurodegenerative diseases, although OPN mRNA has been shown to be expressed in the substantia nigra (SN) in the rat and, therefore, it is possible that OPN may be involved in the pathogenic processes that occur in PD.

OPN is able to regulate cytokine levels and act as a glial cell activator and chemoattractant. There is also evidence for an inflammatory aspect in the pathogenesis of PD. However, it is not yet known whether glial cell activation is a cause or a consequence of neurodegeneration in PD.

SUMMARY OF THE INVENTION

The present inventors have shown that OPN is functionally important in the control of inflammatory changes in neurodegeneration. More particularly, the present inventors have demonstrated that intranigral injection of lipopolysaccharide (LPS) induces a rapid and marked gliosis that accompanies the loss of TH-positive neurones and suggest that, following glial cell activation, there is enhanced expression of OPN linked to increased numbers of microglia and/or macrophages.

The inventors have also demonstrated that administration of an anti-osteopontin (OPN) antibody can induce dopaminergic, or tyrosine hydroxylase (TH), neuron degeneration in a dose-dependent manner, indicating for the first time that endogenous OPN has a role to play in preventing neurodegeneration. The present inventors have also shown that exogenous OPN has no effect on the number of TH positive neurons in rat primary ventral mesencephalic cell cultures but that it can inhibit MPP+ induced death of TH positive neurons. They have also demonstrated that the neuroprotective effects of OPN are not mediated via $\alpha_v\beta_3$ integrin receptors.

BRIEF DESCRIPTION OF THE SEQUENCES

Figure 1:
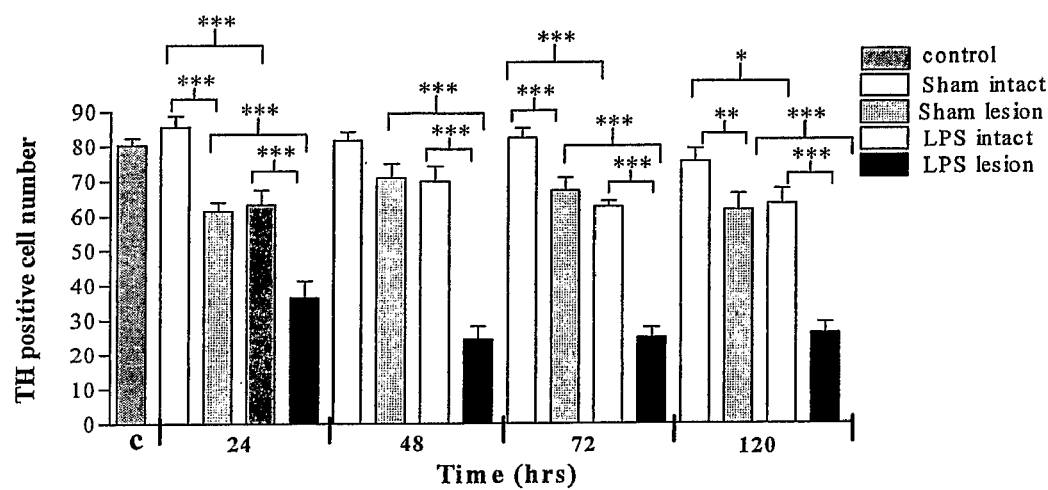
FIG. 1 shows the effect of intranigral administration of LPS on the number of TH immunoreactivite cells in the rat SN. LPS decreased TH cell number in the injected SN (LPS lesion) that was persistent at all the time points studied. TH immunoreactivity was also reduced in the SN contralateral to injection side (LPS intact). Injection of saline produced a small but significant decrease in TH cell number in the ipsilateral (sham lesion) SN. *$p<0.01$, $p<0.01$, *$p<0.05$; One Way ANOVA and Newman Keuls multiple comparison test.

SEQ ID NO: 1 is the nucleotide sequence encoding human osteopontin.

SEQ ID NO: 2 is the amino acid sequence of full-length human osteopontin.

SEQ ID NO: 3 is the amino acid sequence of a thrombin cleavage fragment of human osteopontin.

SEQ ID NO: 4 is the sequence of a 15 amino acid fragment of human osteopontin which is effective in inhibiting neurodegeneration.

SEQ ID NO: 5 is the nucleotide sequence encoding rat osteopontin.

SEQ ID NO: 6 is the amino acid sequence of full-length rat osteopontin.

SEQ ID NO: 7 is the amino acid sequence of a thrombin cleavage fragment of rat osteopontin.

SEQ ID NO: 8 is the amino acid sequence of a 15 amino acid fragment of rat osteopontin which is effective in inhibiting neurodegeneration.

SEQ ID NO: 9 is the consensus amino acid sequence of the human and rat osteopontin fragments shown in SEQ ID NO: 4 and SEQ ID NO: 8.

SEQ ID NOS: 10 to 13 are the nucleotide sequences of olionucleotides used for in situ hybridisation.

DETAILED DESCRIPTION OF THE INVENTION

The present invention provides a method of treating or preventing neurodegeneration in a subject in need thereof, which method comprises the step of administering to the subject a therapeutically effective amount of a polypeptide which is an N- and/or C-terminally truncated fragment of SEQ ID No: 2 or SEQ ID No: 2 species variant, and which has the amino acid sequence shown in SEQ ID No: 9 in a position corresponding to amino acids 138 to 152 of SEQ ID No: 2, or a polynucleotide encoding said polypeptide.

Alternatively, a polynucleotide encoding the osteopontin polypeptide may be administered to the subject. The polynucleotide encoding the osteopontin polypeptide is preferably operably linked to one or more control sequences and is more preferably present in an expression vector.

Polypeptide

The polypeptide comprises the amino acid sequence shown in SEQ ID NO: 9, which is the consensus amino acid sequence of the human and rat osteopontin fragments shown in SEQ ID NO: 4 and SEQ ID NO: 8. SEQ ID NO: 8 is the sequence of a 15 amino acid fragment from rat OPN that is effective in inhibiting neurodegeneration. SEQ ID NO: 4 shows the amino acid sequence of the corresponding 15 amino acid fragment of human osteopontin. Longer N- and/or C-terminally truncated fragments of SEQ ID No: 2 or SEQ ID No: 2 species variant (such as the rat species variant of SEQ ID No: 6) and which have the amino acid sequence shown in SEQ ID No: 9 in a position corresponding to amino acids 138 to 152 of SEQ ID No: 2 example positions 137 to 151 of the rat SEQ ID No: 6). The degree of truncation at the N- or C-terminus of SEQ ID No: 2 or SEQ ID No: 2 variant may be such as to result in, for example, a fragment of 16, 18, 20, 25, 30, 40, 50, 100 or more amino acids in length. The fragments of the human or rat OPN sequences produced by cleavage with Thrombin (SEQ ID NO: 3 or SEQ ID NO: 7), and which have SEQ ID No: 9 in a position corresponding to amino acids 138 to 152 of SEQ ID No: 3 or 137 to 152 of SEQ ID No: 7 are examples of longer fragments for use in the invention, but of course even those longer fragments may be N- and/or C-terminally truncated provided they retain the minimum SEQ ID No: 9.

Species variants of SEQ ID No: 2 variants include the OPNs of the rat, mouse or non-human primates such as the marmoset or monkey.

Polypeptides which typically have at least 70%, preferably at least 80, 90%, 95%, 97% or 99% identity to those defined above, outside the part corresponding to SEQ ID No:9, may be used, and are considered also to be within the scope of the invention.

Amino acid identity may be calculated using any suitable algorithm. For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Polypeptides differing from those defined above by at least 1, 2, 5, 10, 20 or more mutations outside the part corresponding to SEQ ID No:9 (which may be substitutions, deletions or insertions of nucleotide or amino acids) may be used, and are considered also to be within the scope of the invention. The substitutions are preferably conservative substitutions. These are defined according to the following Table. Amino acids in the same block in the second column and preferably in the same line in the third column may be substituted for each other:

| ALIPHATIC | Non-polar | G A P |
| --- | --- | --- |
|  |  | I L V |
|  | Polar - uncharged | C S T M |
|  |  | N Q |
|  | Polar - charged | D E |
|  |  | K R |
| AROMATIC |  | H F W Y |

Polypeptides of the invention are typically produced by recombinant means, enzymatically truncated naturally produced osteopontin may also be used. Recombinantly produced osteopontin polypeptides differ from naturally produced osteopontin in degree of phosphorylation.

A recombinant osteopontin polypeptide may be produced by transfecting mammalian cells in culture with an expression vector comprising a nucleotide sequence encoding the polypeptide operably linked to suitable control sequences, culturing the cells, extracting and purifying the osteopontin polypeptide produced by the cells.

The OPN polypeptide may be chemically modified, e.g. post-translationally modified. For example, it may be glycosylated, phosphorylated or comprise modified amino acid residues.

Polynucleotides

A polynucleotide encoding an OPN polypeptide or variant may be used to treat or prevent neurodegeneration. The OPN polynucleotide may have the nucleotide sequence shown in SEQ ID NO: 1 or be a variant or fragment of at least 45 nucleotides thereof. The variant typically has at least 70%, 80%, 90%, 95%, 98% or 99% sequence identity to the nucleotide sequence of SEQ ID NO: 1 over a region of at least 45 contiguous nucleotides. Sequence identity may be determined by any suitable method, for example, as described above. The polynucleotide is typically included in an expression vector.

Expression vectors capable of expressing an OPN polypeptide may also comprise appropriate initiators, promoters, enhancers and other elements, such as for example polyadenylation signals which may be necessary, and which are positioned in the correct orientation, in order to allow for protein expression.

Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be, for example, a plasmid or virus vector. The vector is typically adapted to be used in vivo.

Promoters and other expression regulation signals may be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR).

The vector may further include sequences flanking the polynucleotide giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Neurodegeneration

The OPN polypeptide, or polynucleotide, may be used to treat or prevent neurodegeneration, preferably age-related neurodegeneration. The neurodegeneration is typically in the CNS. Preferably the neurodegeneration is of dopaminergic neurons. The dopaminergic neurons are typically found in the basal ganglia, which consist of the striatum (candate nucleus and putamen), the globus pallidus, the subthalanic nucleus and the substantia nigra (substantia nigra pars compacta and pars reticula). Preferably the dopaminergic neurons are in the substantia nigra, more preferably in the substantia nigra pars compacta.

The neurodegeneration may be a result of normal ageing. The OPN polypeptide or polynucleotide may be administered to a subject showing signs of age-related neurodegeneration. Alternatively, the OPN polypeptide may be administered to a subject to prevent age-related neurodegeneration. In this embodiment, the subject is typically more than 60, 65, 70, 75 or 80 years old.

Preferably, the neurodegeneration is in a subject with a neurodegenerative disorder or in a subject with a genetic predisposition to a neurodegenerative disorder.

The neurodegenerative disorder is typically one that involves inflammatory changes and/or pathogenic processes underlying cell death that are similar to those in Parkinson's disease.

The neurodegenerative disorder may be multiple sclerosis, motor neurone disease, Huntington's chorea or Alzheimer's disease.

The neurodegenerative disorder is typically one associated with loss of dopaminergic neurons, such as Parkinson's disease, dementia of the Lewy body type or a Parkinson-plus syndrome. Parkinson-plus syndromes include multiple system atropy (MSA) and progressive supranuclear party (PSP). The neurodegenerative disorder may be, for example, sporadic Parkinson's disease, a familial form of Parkinson's disease or post-encephalitic Parkinson's disease.

The main symptoms of Parkinson's disease are tremor, rigidity of the limbs and trunk, akinesia, bradykinesia and postural abnormalities. A therapeutically effective amount which, when administered to a subject having Parkinson's disease, or a Parkinson-plus syndrome, ameliorates or lessens the severity of one or more of the symptoms of the disease.

The OPN polypeptide or polynucleotide may be administered to an individual in order to prevent the onset of one or more symptoms of the disease. In this embodiment, the subject may be asymptomatic. The subject may have a genetic predisposition to the disease. A prophylactically effective amount of the polypeptide or polynucleotide is administered to such an individual. A prophylactically effective amount is an amount which inhibits neurodegeneration, typically degeneration of dopaminergic neurons, and hence prevents the onset of one or more disease symptoms.

The subject is typically a mammalian subject, such as a mouse, rat or primate (e.g. a marmoset or monkey). The subject may be human or a non-human animal. Where the subject is a laboratory animal such as a mouse, rat or primate, the animal may be treated to induce neurodegeneration: for example lipopolysaccharide (LPS) may be used to activate glial cells and induce neurodegeneration, such as nigral neuronal degeneration. Other animal models of Parkinson's disease include the 6-hydroxydopamine (6-OHDA) lesion model (preferably a rat model) and the 1-methyl-4-phenyl-1, 2,3,6-tetrahydropyridine (MPTP) model (preferably a non-human primate model).

The animal model of Parkinson's disease may be induced by administering an anti-OPN antibody to the brain. Preferably, the anti-OPN antibody is injected into the basal ganglia of the animal. Disease models may be generated using OPN antisense sequences or RNAi technology. The animal model of Parkinson's disease may be a transgenic mouse, such as an OPN-knockout mouse.

Administration

The OPN polypeptide may be administered to the subject by any suitable means. Small peptides, for example peptides of from 15 to 50 amino acids, that can cross the blood brain barrier may be administered systemically. Alternatively, these peptides may be delivered directly to the brain or the ventricular system, for example by infusion or injection.

The formulation of any of the therapeutic substances mentioned herein will depend upon factors such as the nature of the substance and the condition to be treated. Any such substance may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The substance may also be administered as suppositories. A physician will be able to determine the required route of administration for each particular patient.

Typically the substance is formulated for use with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of substance is administered. The dose may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The following Examples illustrates the invention:

EXAMPLES

Given that OPN is present in the substantia nigra and that it possesses a range of anti-inflammatory properties, we have investigated whether OPN is induced by inflammation in the rat substantia nigra resulting from intranigral injection of LPS.

Materials and Methods

Animals

Male Wistar rats (250-280 g) were obtained from Tuck (Essex, UK) and were kept on a 12 hour light/dark cycle at 21-24° C. with 55-65% humidity with unrestricted access to rat chow and water. All experiments were conducted according to the guidelines set out in the UK Animals (Scientific Procedures) Act 1986 and approved by the King's College London Ethics Committee.

Surgery

Animals were randomly divided into 4 groups (n=16 in each group) anaesthetised with halothane (4% in 5%$O_2$: 95%$CO_2$), placed in a stereotaxic frame (Kopf Instruments) with the incisor bar set at −3.3 mm and anaesthesia maintained using halothane (1.5-2%). The heads were shaved, scalp cut, skull exposed and a burr hole drilled on the left side of the skull. The following co-ordinates for the SN were used: AP: −4.8 mm, L: +2.0 mm, V: +8.0 mm (Paxinos & Watson, 1986). A 10 μl Hamilton syringe was used and 2 μl of LPS (n=8) (5 mg/ml dissolved in 0.9% sterile saline: E. coli 055: B5; Calbiochem, Nottingham, UK) or 2 μl of vehicle (0.9% sterile saline; n=8) was delivered over a period of 2 minutes. The needle was left in situ for a further 2 minutes before being slowly withdrawn. The wound was closed using Ethicon sutures and the animals allowed to recover from anaesthesia until freely moving before being returned to their home cages.

Tissue Preparation

Each group of rats were killed at one of the following time points post surgery: 24, 48, 72 or 120 hours. Untreated rats were used as a control group. The rats were terminally anaesthetised with sodium pentobarbitone (Sagatal; 100 mg/kg i.p.) and transcardially perfused with 0.1M phosphate buffered saline (PBS) followed by 4% paraformaldehyde in 0.1M PBS. The brains were removed and post-fixed for 24 hrs at 4° C. in 4% paraformaldehyde. The tissue was then transferred into 30% sucrose solution containing 0.05% sodium azide and stored at 4° C. until the tissue had equilibrated. Subsequently the tissue was snap frozen at −45° C. in isopentane and stored at −70° C. Coronal sections of tissue (30 μm) were cut at −20° C. using a Bright cryostat (Bright Instruments Company Ltd, Huntington, U.K.), and stored as free-floating sections in 0.1M PBS containing 0.05% sodium azide at 4° C. for immunohistochemical use. For in situ hybridisation, coronal sections of tissue (18 μm) from the same animals were thaw-mounted onto polylysine coated slides and stored at −70° C.

In situ Hybridisation

The following oligonucleotides to the OPN sequence were designed:

Gatgtcgtagactcacaaagcacattacgcggaagaggag (SEQ ID NO: 10), acacccccgctaacctcagttttgcagacgaacacacgac (SEQ ID NO: 11), gatcctgatcgaacaggagtaccgacactttgagcaggca (SEQ ID NO: 12), gcgcctccactccaggagtagacaccgtagccctatgaca (SEQ ID NO: 13), (Accession Number: M14656) and used at a working concentration of 50 ng/µl as previously described (Iczkiewicz et al., 2004). In situ hybridisation was performed based on the protocol of (Zeng et al., 1995). Briefly, each probe (150 ng) was labelled in a mixture of 5× buffer, DEPC $H_2O$, $^{35}$S-dATP (1250 Ci/mM, NEN) and terminal deoxynucleotidyl transferase (3U, Promega, Southampton, UK) at 37° C. for 90 mins. The reaction was terminated by the addition of Tris EDTA buffer (10 mM) and the probes purified using a Nick column. The total incorporation of radioactivity was measured using a scintillation counter (Packard, Berks, UK). Slide-mounted sections of rat brain and kidney were fixed in 4% paraformaldehyde, incubated in 0.25% acetic anhydride, dehydrated through 70%, 80%, 95% and 100% ethanol solutions, delipidated in chloroform and then air dried. A mixture of all of the 4 labelled oligonucleotides was diluted in hybridisation buffer (50% formamide, 10% dextran sulphate, 20×SSC, 2% salmon sperm DNA, 2% 1M DTT, 2% Denhardt's solution, 2% Poly A acid) and 50 µl of this mixture was placed on each section and covered with parafilm. Slides were incubated overnight at 37° C. in a moisture box. The slides were then washed four times with 1×SSC at 55° C. for 15 mins and then twice at room temperature with 1×SSC for 30 mins before being air dried and then apposed along with $^{14}$C standards (Amersham) to film for 2 weeks. The films were analysed by computerised densitometry (MCID; Image Research Inc.). A calibration curve was generated by measuring the $^{14}$C standards, plotting against known disintegrations per minute per mg, and converting to $^{35}$S equivalence. For each section the SN was outlined and the optical density of the outlined area was converted to nCi/µg wet weight of tissue from the calibration curve and the values obtained used for statistical analysis. Non-specific signal, as assessed using RNAse-treated sections, was subtracted from the obtained values which were then pooled to obtain mean values for each group.

Peroxidase Immunohistochemistry

The free-floating sections were incubated in a solution of 30% $H_2O_2$ in 70% methanol for 30 mins followed by an hour long incubation in 20% normal goat serum (NGS) in 0.1M PBS. The sections were then permeabilised in 0.1M PBS/1% NGS/0.05% Triton X-100 prior to overnight incubation at room temperature in a 0.1M PBS/1% NGS solution containing one of the following antibodies: mouse anti-rat OPN antibody (1:500, MPIIIB10$_1$, Developmental Studies Hybridoma Bank, University of Iowa, U.S.A.), mouse anti-rat OX-42 (1:100, Serotec, Oxford, UK), mouse anti-rat ED1 (1:500, Serotec, Oxford, UK), rabbit anti-rat TH (1:500, Pel-Freeze Biologicals, AR, USA) and rabbit anti-rat GFAP (1:500, Promega, Southampton, UK). ED1 recognises activated phagocytic macrophages/microglia and OX-42 recognises the CR3 complement receptor on microglial cells. Goat anti-mouse biotinylated secondary antibody (1:200, Jackson Immunoresearch Labs, PA, USA) was applied to the sections incubated with mouse antibodies and goat anti-rabbit secondary (Vector Laboratories, Peterborough, UK ) was used for sections incubated with rabbit antibodies for 1 hr following two 5 min washes in 0.1M PBS. This was followed by incubation in avidin-biotin complex (1:200, ABC, Vector Laboratories, Peterborough, UK) for an hour. Visualisation of the immunoreactive products was performed through a 10 min incubation of the sections in 0.05% 3,3'-diaminobenzidine (DAB) in 0.05M Tris HCl and 1% $H_2O_2$. For double labelling immunohistochemistry using primary antibodies raised in the same species, sections were first incubated with the OPN antibody with DAB used as the chromagen (brown staining) and then with the second primary antibody (OX-42 or ED1) using VIP (Vector Laboratories, Peterborough, UK) as the chromagen (purple staining). The sections were then mounted onto polylysine coated slides, dehydrated through 70%, 96%, 100% ethanol solutions, cleared in Histoclear (BDH, Dorset, UK) and coverslipped with DPX mounting medium (BDH, Dorset, UK). A Zeiss Axioskop microscope was used to examine the sections.

Double Labelling Fluorescence Immunohistochemistry

Free-floating sections were incubated in 20% NGS solution in 0.1M PBS for 1 hr followed by two 5 min washes in 0.1M PBS/1% NGS/0.05% Triton X-100. The sections were then incubated overnight in 0.1M PBS/1% NGS containing a mixture of both mouse anti-rat OPN (1:500) and rabbit anti-rat GFAP (1:500) antibodies and visualised by incubation for 2 hours in a darkened environment with a mixture of a secondary antibody conjugated with FITC (green, Jackson Immunoresearch Laboratories, PA, USA) and a secondary antibody conjugated with Texas Red (red, Vector Laboratories, Peterborough, UK) (1:100). After three 30 min washes in 0.1M PBS the sections were mounted onto polylysine coated slides and coverslipped with Vectashield mounting medium (Vector Laboratories, Peterborough, UK) in a darkened environment.

Statistics

Data was analysed using a One Way ANOVA and post hoc analysis using a Newman Kuels test to compare data between treatment groups at each time point studied. Comparisons were made between untreated control animals, saline treated and LPS treated animals. Data was expressed as mean±SEM, $p<0.05$ was considered significant.

Example 1

Nigral Cell Death Following Intranigral LPS Administration

Injection of saline into the SN produced a small decrease in TH cell number compared to the contralateral SN (sham intact) (FIG. 1). Intranigral LPS administration resulted in nigral cell death as shown by a 70% decrease in TH positive cells in the LPS injected SN compared to the contralateral intact SN and to saline controls (FIG. 1). The reduction in TH positive cells was present at all time points studied (24, 48, 72 and 120 hrs). LPS treatment also produced a small reduction in TH positive cell number in the contralateral SN (LPS intact).

Example 2

Gliosis Following Intranigral LPS Injection

The reduction in TH cell number was accompanied by an inflammatory gliosis as shown by increases in the number of ED1 positive, OX-42 positive and to a lesser extent GFAP positive cells.

ED1 Immunoreactivity

Figure 2:
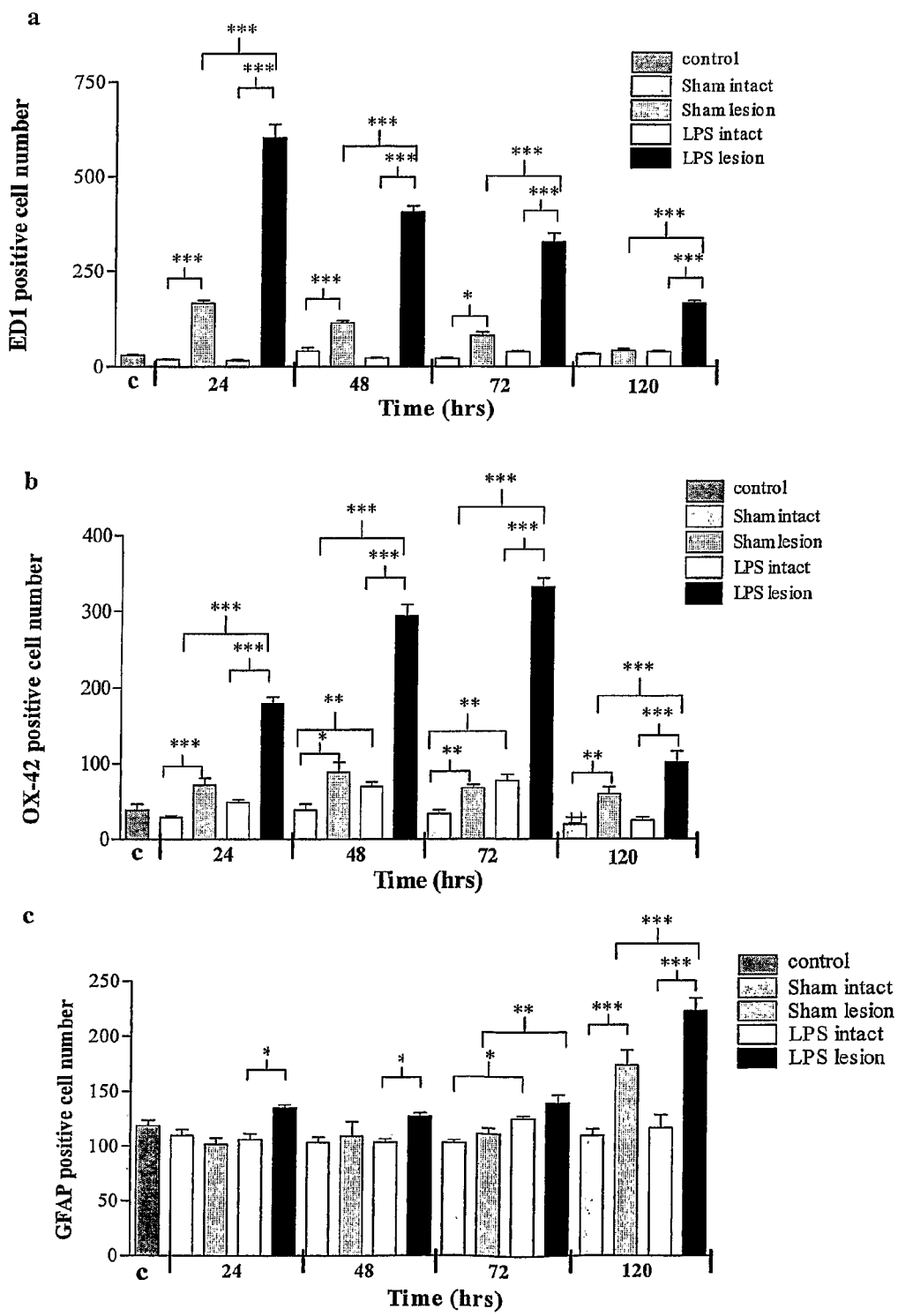
FIG. 2 shows the effect of intranigral administration of LPS on the number of ED1, OX-42 and GFAP positive cells in the rat SN. (a) LPS increased ED1 cell number in the injected SN (LPS lesion) in a time dependent manner peaking at 24 hours post LPS administration. Injection of saline also produced a significant increase in ED1 cell number in the ipsilateral (sham lesion) SN. No increase in ED1 immunoreactivity was present in the contralateral SN following either LPS or saline injection. (b) LPS increased OX-42 cell number in the injected SN (LPS lesion) in a time dependent manner peaking at 72 hours post LPS administration before returning to baseline levels. Injection of saline produced no significant changes in OX-42 positive cell number in the ipsilateral (sham lesion) SN. In contrast, OX-42 positive cell number decreased in the contralateral SN following both LPS (LPS intact) and saline (sham intact) injection. (c) LPS increased GFAP cell number in the injected SN (LPS lesion) in a time dependent manner peaking at 120 hours post LPS administration at the time points studied. Injection of saline produced an increase in GFAP positive cell number that only became apparent at 120 hours post injection. No changes in GFAP immunoreactivity were seen in the contralateral SN following either LPS (LPS intact) or saline (sham intact) injection. *$p<0.01$, $p<0.01$, *$p<0.05$; One Way ANOVA and Newman Keuls multiple comparison test.

Intranigral injection of saline resulted in a small increase in ED1 positive cells in the treated SN which peaked at 24 hours before returning to baseline by 120 hours. In contrast, following LPS administration, the number of ED1 positive cells increased rapidly and peaked at 24 hours post injection. This rise then gradually declined although a significant number of ED1 positive cells were still present throughout the SN at 120 hours (FIG. 2a). The effect on ED1 positive cells was localised to the LPS injected SN and no increase in ED1 immunoreactivity was observed in the contralateral intact SN.

OX-42 Immunoreactivity

Injection of saline resulted in an increase in OX-42 immunoreactivity in the lesioned SN which peaked at 48 hours and persisted both 72 and 120 hours post-injection. Following LPS administration, OX-42 positive cell numbers increased throughout the SN, although more gradually than observed for ED1 positive cells with levels peaking at 72 hours. The number of OX-42-immunoreactive cells subsequently decreased and levels still persisted at 120 hours (FIG. 2b).

GFAP Immunoreactivity

Intranigral saline injection resulted in a small increase in GFAP positive cells at 120 hours (FIG. 2c). Following intranigral LPS administration, astrocytosis accompanied nigral cell death although it occurred more slowly than the rise in either ED1 or OX-42 positive cells. Increased expression of GFAP in the injected SN only became apparent at 24 hours post LPS injection with the highest levels at 120 hours (FIG. 2c). No increase was seen in the intact SN following LPS administration.

Example 3

Effect of Intranigral LPS Administration on OPN Expression in the SN

OPN mRNA Expression

Figure 3:
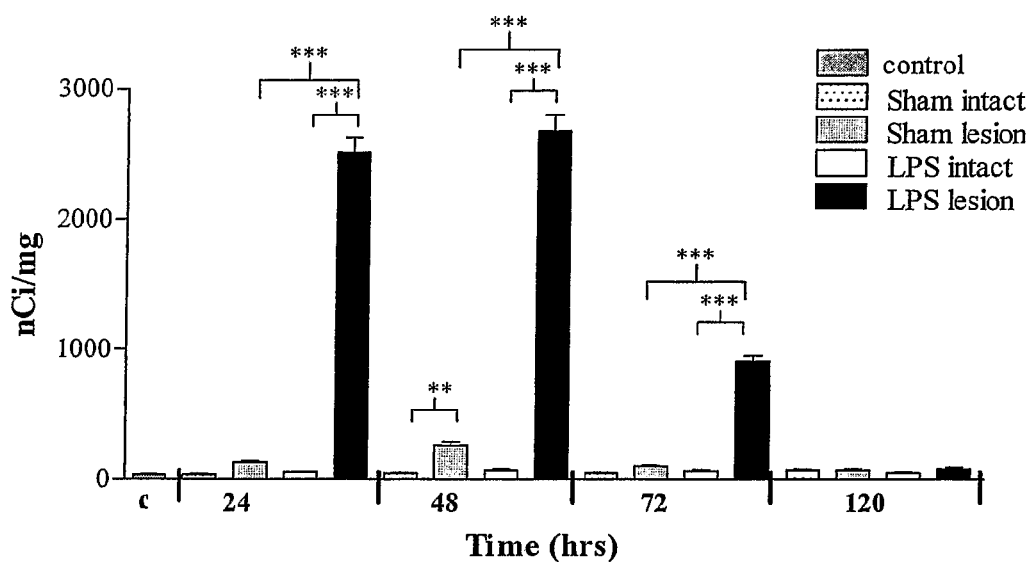
FIG. 3 shows the effect of intranigral administration of LPS on OPN mRNA expression in the SN of rat. LPS increased OPN expression in the injected SN (LPS lesion) in a time dependent manner before returning to baseline levels at 120 hours. No changes were seen in the SN contralateral to injection side (LPS intact). Injection of saline did not produce any significant increase in OPN expression in either ipsilateral (sham lesion) or contralateral SN (sham intact). *$p<0.001$; $p<0.01$ One Way ANOVA and Newman Keuls multiple comparison test.

Intranigral injection of saline produced no significant change in OPN mRNA expression at any time point. No changes in OPN mRNA expression were seen in the intact SN following saline administration. Following intranigral LPS administration, OPN was significantly up-regulated as shown by the increase in mRNA expression at 24 hours (FIG. 3). OPN expression peaked at 48 hours, decreased at 72 hours before returning to baseline levels by 120 hours. No changes in OPN mRNA expression were detected in the intact SN.

OPN Immunoreactivity

Figure 4:
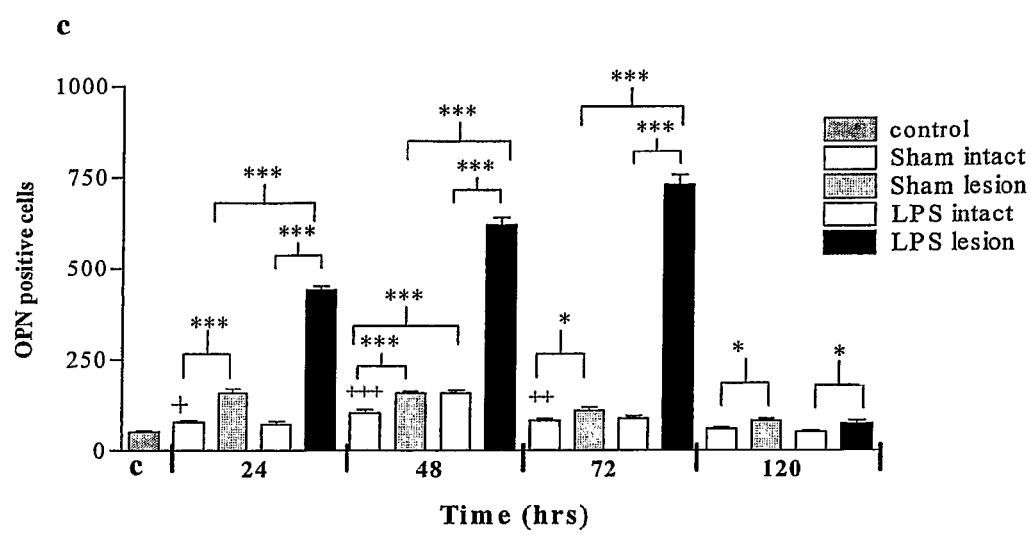
FIG. 4 shows the effect of intranigral administration of LPS on extracellular and intracellular OPN immunoreactivity in the rat SN. LPS increased OPN immunoreactivity in the injected SN (LPS lesion) in a time dependent manner before returning to baseline levels at 120 hours. OPN immunoreactivity also increased at 48 hours in the SN contralateral to injection side (LPS intact). Injection of saline produced a small but significant increase in OPN immunoreactivity in both the ipsilateral (sham lesion) and contralateral SN (saline intact). $^{+++}p<0.001$, $^{++}p<0.01$, $^{+}p<0.05$ compared to control; *$p<0.01$, $p<0.01$, *$p<0.05$; One Way ANOVA and Newman Keuls multiple comparison.

Intranigral injection of saline produced a small increase in OPN immunoreactivity in the treated SN compared to the contralateral SN (sham intact) as well as increasing immunoreactivity in the contralateral SN compared to control (FIG. 4). OPN staining was unilateral at the site of LPS injection and extracellular and intracellular OPN was present throughout the SN. OPN was prominent around the injection site as well as throughout the SN. Following LPS administration, OPN immunoreactivity increased 14-fold compared to saline treated animals. OPN levels rose steadily in the LPS injected SN and peaked at 72 hours post injection before returning to baseline by 120 hours (FIG. 4). OPN immunoreactivity also increased in the intact contralateral SN of the LPS treatment group at 48 hours.

OPN Co-Localisation Following Intranigral LPS Injection

OPN immunoreactivity was present both extracellularly and intracellularly in the lesioned SN following LPS injection. Small OPN aggregates co-localised with both ED1 positive cells and OX-42 positive cells at 24, 48 and 72 hours throughout the SN and surrounding the injection site. No co-localisation between OPN and either ED1 or OX-42 was seen at 120 hours post-injection. OPN did not co-localise with GFAP positive cells or with TH positive cells (results not shown) at any of the time points studied.

Examples 4 to 7

The following experiments aim to investigate what function OPN may play in the degeneration of dopaminergic neurones. The experiments to date have involved the use of in vitro primary ventral mesencephalic cell cultures subjected to neurotoxic insult in order to see whether OPN has an effect on the survival of the dopaminergic neurones in these cultures.

Materials and Methods

Primary ventral mesencephalic cell cultures: Primary cell cultures were prepared by dissecting out the ventral mesencephalon from E14 rat foetuses. The dissected tissue was pooled and incubated with 0.1% Trypsin solution. This solution was then removed and replaced with Dulbecco's modified Eagles medium (DMEM) containing 10% foetal bovine serum (FBS) and 0.25% penicillin-streptomycin-neomycin (PSN), and the tissue centrifuged for 1 minute at 200 rpm at room temperature. The supernatant was then removed, fresh medium was added and the tissue mechanically dissociated using increasing fine bore fire-polished Pasteur pipettes. Cell density was assessed using a haematocytometer and cells were plated in culture medium containing 10% FBS and 0.25% PSN at a density of $1\text{-}1.5\times10^5$ on sterile coverslips coated with 0.01% poly-D-lysine. After 4 days the culture medium was removed and replaced with fresh serum free DMEM prior to treatment with MPP+ or OPN. Each treatment was done in triplicate per experiment and each series of experiments was repeated a further 2 times to give a final n=3.

MPP+ dose response: MPP+ was dissolved in sterile PBS and the primary cell cultures were incubated for 24 hrs with one of the following concentrations of MPP+: 0.1, 0.5, 1, 2, 5, 10 µM MPP+ or vehicle (PBS). A control group received no treatment. An EC50 was calculated (3.076±0.56) and a high (10 µM) or low (2 µM) MPP+ concentration was used to investigate the role of OPN in dopaminergic cell survival.

Manipulation of the OPN system: Cultures were incubated with one of the following treatments for 24 hrs prior to MPP+ administration (either 10 µM or 2 µM MPP+): OPN protein (1, 5, 10, 25, 50 & 100 ng/ml), anti-OPN antibody (26.5, 53, 265, 530 ng/ml and 1.325, 2.65 µg/ml), anti-$\alpha_v$ or anti-$\beta_3$ integrin receptor subunit antibody (0.02, 0.04, 0.2, 0.4, 1 & 2 µg/ml). Control groups received no MPP+ treatment.

Tyrosine hydroxylase (TH) immunohistochemistry: The culture medium was removed from the cells and the coverslips were fixed in 4% paraformaldehyde prior to peroxidase detection of TH using the ABC immunohistochemical method. Coverslips were mounted and examined using a Zeiss Axiophot microscope at a 50× magnification and the number of TH positive cells on each coverslip was manually counted in four fields chosen at random.(total area: 8 mm$^2$).

Example 4

Figure 5:
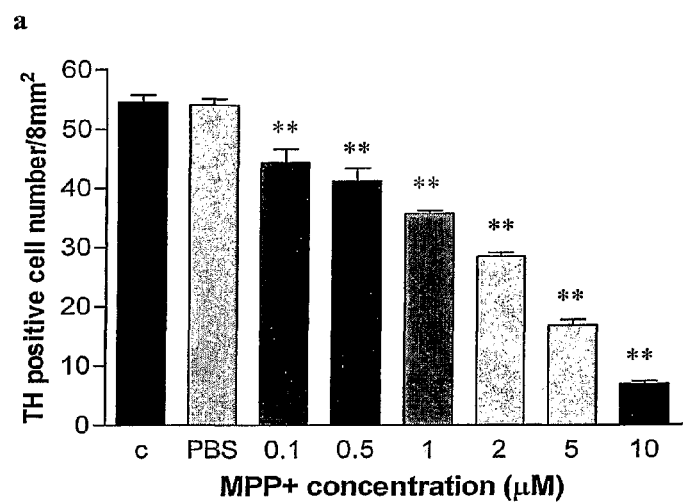
FIG. 5 shows the effect of different MPP+ concentrations on TH positive cell number. Primary ventral mesencephalic cell cultures were exposed to different concentrations of MPP+ 24 hrs prior to fixation for immunohistochemical analysis of TH-immunoreactivity in order to establish an MPP+ dose response curve. (a) MPP+ dose response curve; EC50=3.076, SEM=0.56, n=3; **$p<0.01$ compared to control, (One Way ANOVA and Dunnett's post hoc test) (b) TH-immunoreactivity in control cell cultures and following treatment with low (2 µM) and high (10 µM) concentrations of MPP+. (Arrows show TH positive cells).
Figure 5:
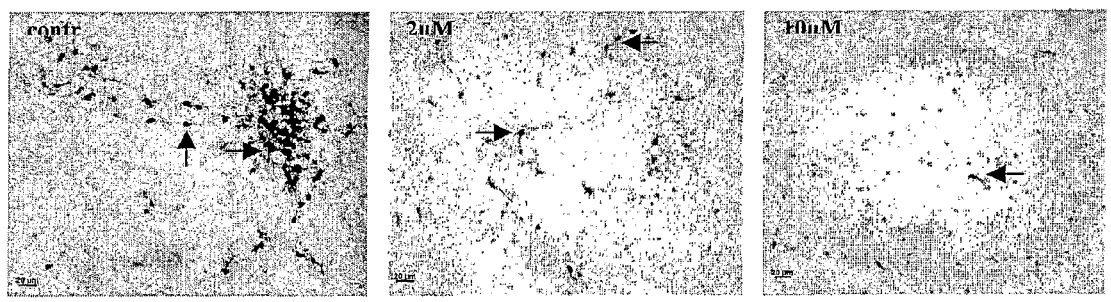

Effect of MPP+ on Dopaminergic Neurones in vitro:

An MPP+ dose response curve was first established in order to ascertain the level of dopaminergic cell death in the ventral mesencephalic primary cell cultures. As shown in FIG. 5 the concentrations of MPP+ used in this investigation resulted in dopaminergic cell death in a dose dependent manner. The EC50 was calculated (3.076±0.56) and both a high and low concentration of MPP+ was used in order to evaluate whether OPN plays a different role, if any, following a substantial cell loss compared to a less substantial cell loss, on the survival of dopaminergic neurones.

Example 5

Figure 6:
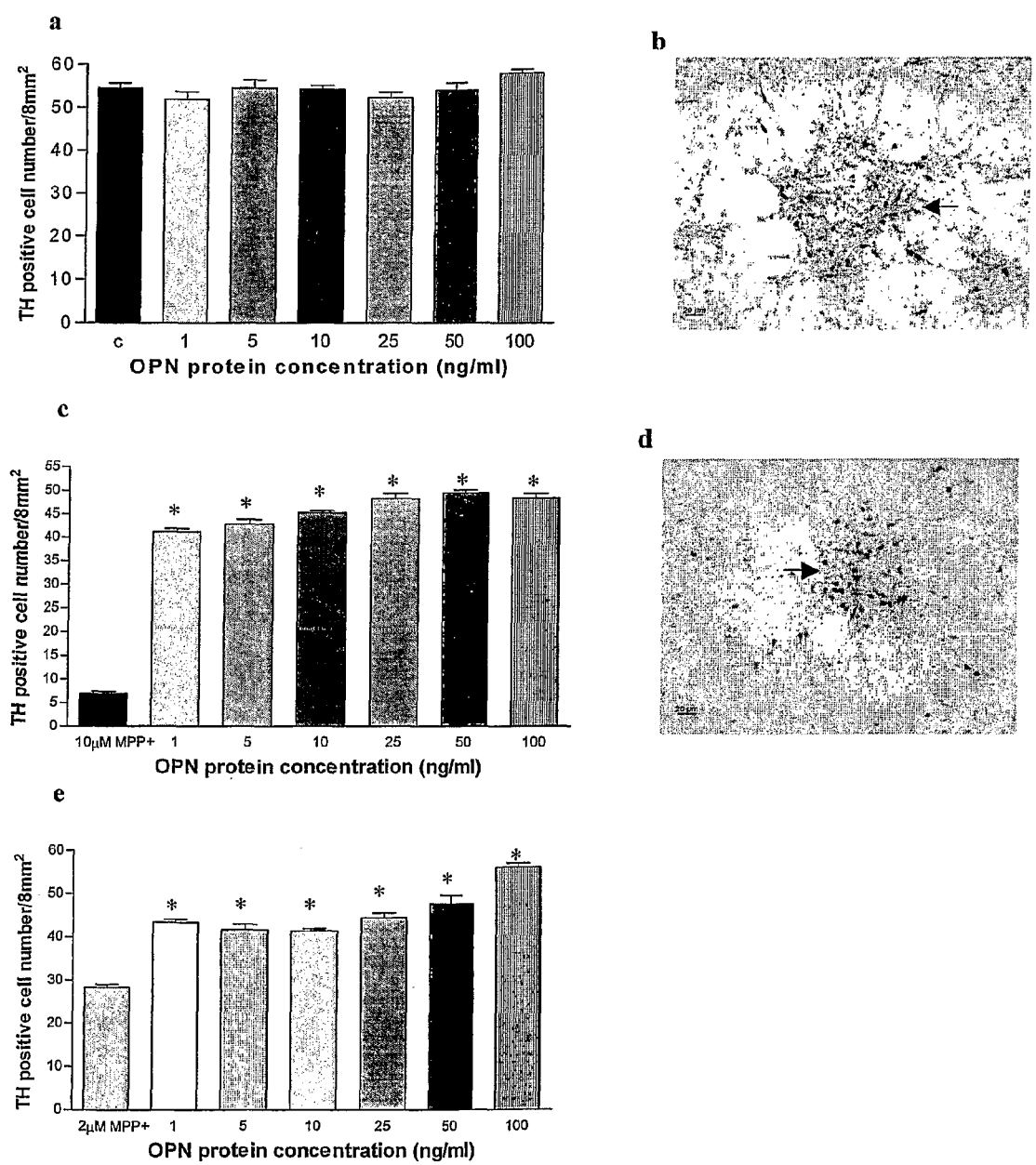
FIG. 6 shows the effect of a rat OPN protein fragment (SEQ ID NO: 8) on the survival of TH positive cells in primary ventral mesencephalic cultures with or without MPP+ treatment. Primary cell cultures were exposed to different concentrations of the rat OPN fragment for 24 hrs prior to fixation for immunohistochemical analysis: (a) Incubation of the cell cultures with OPN had no effect on the viability of TH positive cells at any protein concentration; (b) TH positive cells incubated with 1 ng/ml OPN. Following treatment with OPN, cell cultures were exposed to MPP+ for 24 hrs prior to fixation for immunohistochemical analysis: (c) Following 10 µM MPP+ administration OPN increased survival of TH positive cells reaching maximal efficacy at the lowest OPN protein concentration used (1 ng/ml); $p<0.01$ compared to 10 µM MPP$^+$ control group; (d) TH positive cells incubated with 1 ng/ml OPN followed by 10 µM MPP$^+$ treatment; (e) Following 2 µM MPP+ administration, OPN increased TH cell survival reaching maximal efficacy at 1 ng/ml; $p<0.01$ compared to 2 µM MPP$^+$ control group. (n=3; One Way ANOVA and Dunnett's post hoc test; Arrows show TH positive cells).

Effect of OPN Protein Fragment on Dopaminergic Cell Survival:

Once the MPP+ dose response curve was established the effect of treatment with OPN was investigated. In the first series of experiments, a fragment of the rat OPN protein fragment which contained the RGD $\alpha_v\beta_3$ integrin binding site as well as the binding sites for both the $\alpha_4$ and $\alpha_9$ integrin subunits was added to the primary cultures (SEQ ID NO: 8). The OPN fragment on its own, without the presence of any toxins, was not found to affect the viability of the neuronal cells at any of the concentrations used compared to cells which received no treatment (FIGS. 6a & b).

In contrast, following both 10 μM (FIGS. 6c & d) and 2 μM (FIG. 6e) MPP+ treatment the OPN protein fragment was demonstrated to be equally effective in decreasing dopaminergic cell death at all the concentrations used. The OPN protein reached maximal efficacy at the lowest concentration used (1 ng/ml) and almost completely protected dopaminergic cells to the same extent regardless of the MPP+ concentration.

These results suggest that OPN, and truncated OPNs which contain the tested fragment or species variants thereof, have a protective effect on the dopaminergic neurones following neurotoxic challenge, and that the efficacy of this protein is very high, as maximal effect was seen at 1 ng/ml.

Example 6

Effect of Anti-OPN Treatment on Dopaminergic Cell Survival

In the second series of experiments the effect of blocking OPN was investigated. In the control groups, where no toxin was administered, anti-OPN treatment resulted in a dose-dependent loss of dopaminergic cells (FIG. 7a;

EC50=241±23.6 ng/ml). Cell loss was observed at all of the concentrations of anti-OPN used, and the highest concentration (2.65 μg/ml) resulted in a similar level of cell loss as found following 10 μM MPP+.

Figure 7:
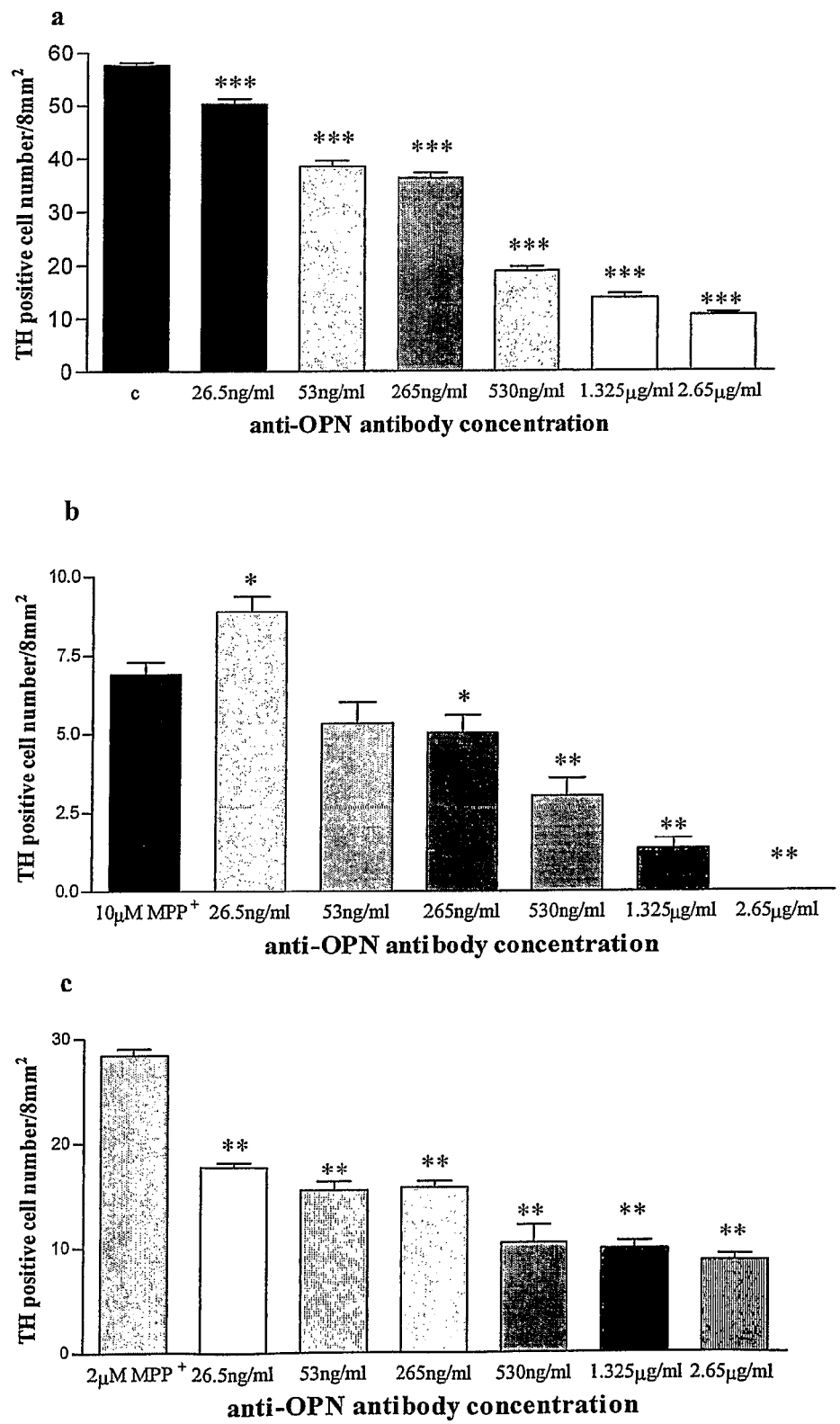
FIG. 7 shows the effect of anti-OPN on the survival of TH positive cells in primary ventral mesencephalic cultures with or without MPP$^+$ treatment. Primary cell cultures were exposed to different concentrations of anti-OPN for 24 hrs prior to fixation for immunohistochemical analysis: (a) Incubation of the cell cultures with anti-OPN increased TH positive cell death in a dose-dependent manner (EC50=809.4 ng/ml, SEM=321.9); *$p<0.001$ compared control group. Following treatment with anti-OPN, cell cultures were exposed to MPP+ for 24 hrs prior to fixation for immunohistochemical analysis: (b) Following 10 µM MPP+ administration anti-OPN exacerbated the death of TH positive cells in a dose-dependent manner (EC50=241 ng/ml, SEM=23.6); $p<0.01$, *$p=0.05$ compared to 10 µM MPP$^+$ control group; (c) Following 2 µM MPP+ administration, anti-OPN increased TH cell death (EC50=22.8 ng/ml, SEM 1.84); **$p<0.01$ compared to 2 µM MPP+ control group. (n=3; One Way ANOVA and Dunnett's post hoc test; Arrows show TH positive cells).

Following MPP+ administration, cell death was exacerbated by treatment with anti-OPN at both of the MPP+ concentrations used. This effect was dose-dependent following 10 μM MPP+ administration (FIG. 7b) although not following 2 μM MPP+ administration (FIG. 7c).

These results suggest that removing the presence of endogenous OPN is detrimental to the survival of dopaminergic ventral mesencephalic neurones, and that this exacerbated the effect of a neurotoxin. These results also confirm the above findings which suggest that OPN is protects dopaminergic cells.

Example 7

Figure 8:
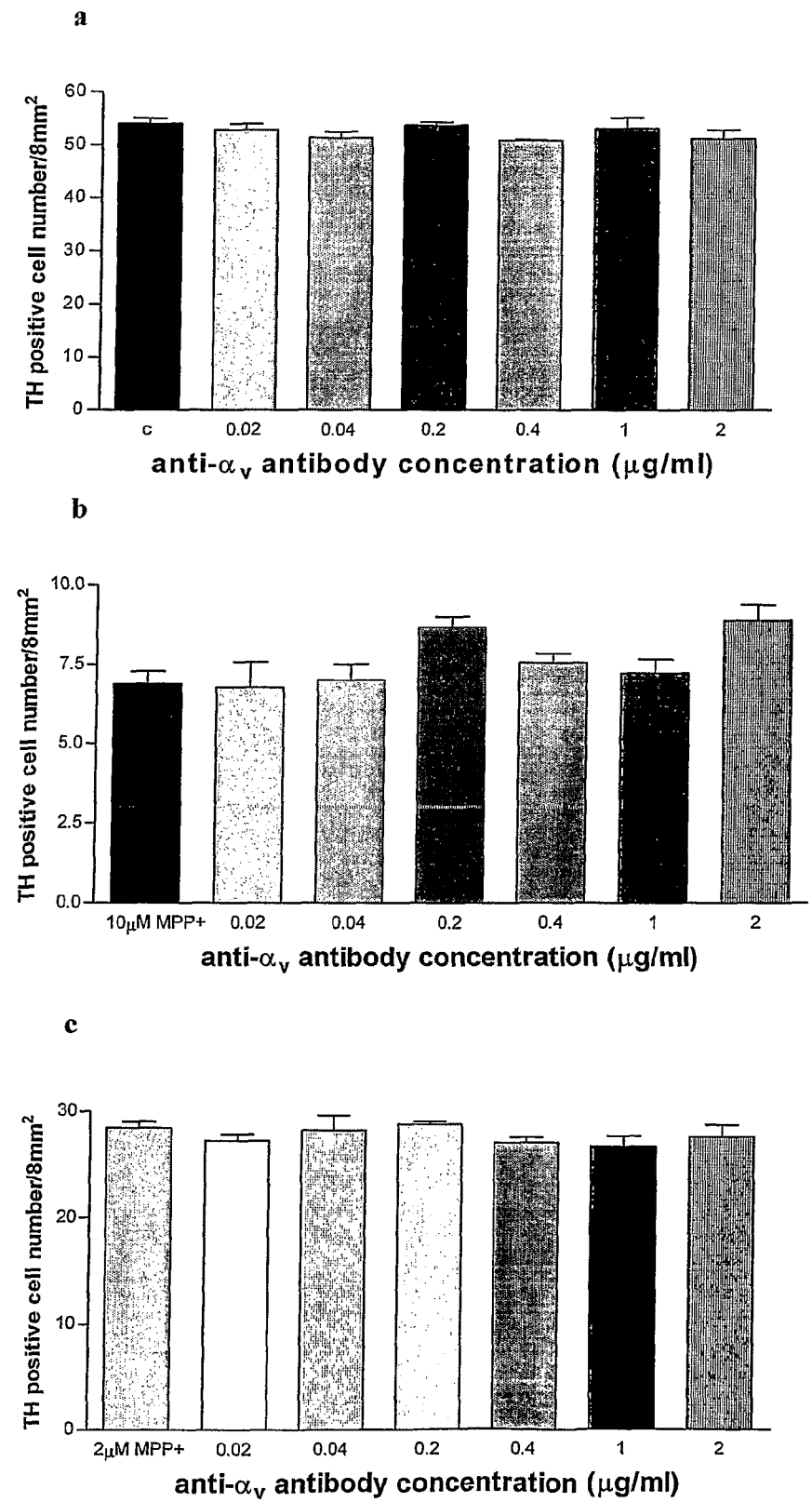
FIG. 8 shows the effect of anti-$\alpha_v$ on the survival of TH positive cells in primary ventral mesencephalic cultures with or without MPP+ treatment. (a) Primary cell cultures were exposed to different concentrations of anti-$\alpha_v$ for 24 hrs prior to fixation for immunohistochemical analysis. Incubation of the cell cultures with anti-$\alpha_v$ had no effect on the viability of TH positive cell death. Following treatment with anti-$\alpha_v$, cell cultures were exposed to MPP+ for 24 hrs prior to fixation for immunohistochemical analysis: (b) Following 10 µM MPP+ administration anti-$\alpha_v$ had no effect on the death of TH positive cells; (c) Following 2 µM MPP+ administration, anti-$\alpha_v$ had no effect on the death of TH positive cells. (n=3; One Way ANOVA).

Effect of Blocking the $\alpha_v\beta_3$ Receptor Subunits on Dopaminergic Cell Death:

In the third series of experiments the effect of blocking the $\alpha_v$ receptor subunit on dopaminergic cell death was investigated. When no toxin was present, anti-$\alpha_v$ had no significant effect on the dopaminergic neurones (FIG. 8a). Similarly, following both high (FIG. 8b) and low (FIG. 8c) concentrations of MPP+, anti-$\alpha_v$ had no effect on dopaminergic cell survival.

Figure 9:
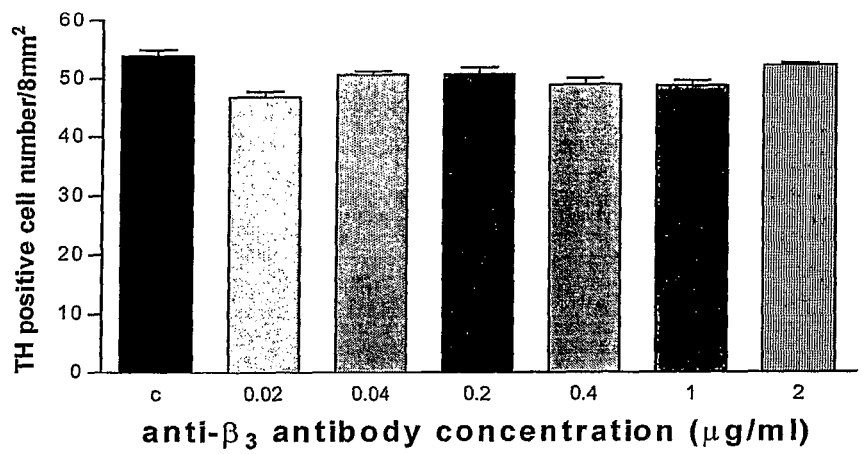
FIG. 9 shows the effect of anti-$\beta_3$ on the survival of TH positive cells in primary ventral mesencephalic cultures with or without MPP$^+$ treatment. (a) Primary cell cultures were exposed to different concentrations of anti-$\beta_3$ for 24 hrs prior to fixation for immunohistochemical analysis. Incubation of the cell cultures with anti-$\beta_3$ had no effect on the viability of TH positive cell death. (b-c) Following treatment with anti-$\beta_3$, cell cultures were exposed to MPP+ for 24 hrs prior to fixation for immunohistochemical analysis. (b) Following 10 µM MPP+ administration anti-$\beta_3$ had no effect on the death of TH positive cells; (c) Following 2 µM MPP+ administration, anti-$\beta_3$ had no effect on the death of TH positive cells. (n=3; One Way ANOVA).
Figure 9:
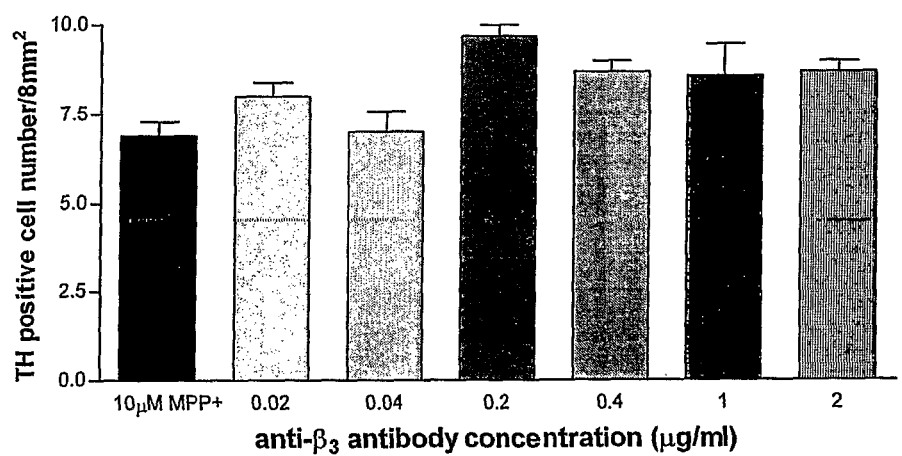
Figure 9:
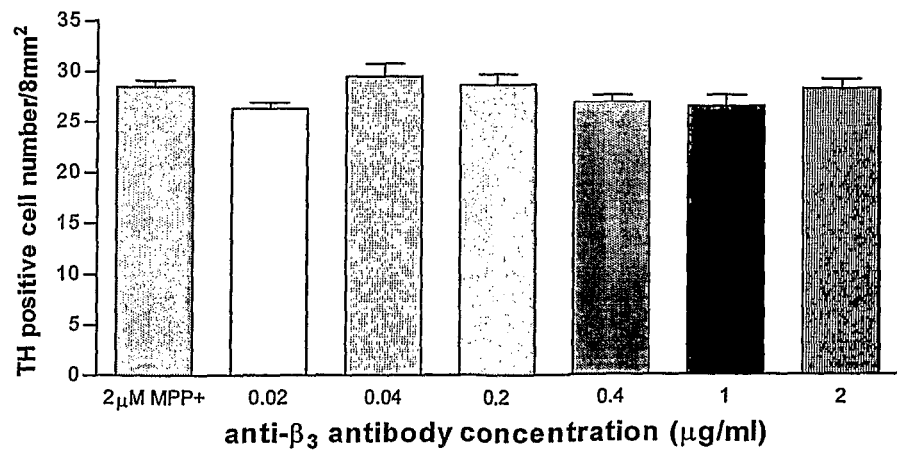

In the fourth series of experiments, the effect of blocking the $\beta_3$ subunit of the integrin receptor was investigated. In control-groups, as with the anti-$\alpha_v$ antibody, blocking the $\beta_3$ integrin receptor subunit had no effect on the viability of dopaminergic cells (FIG. 9a). Similarly to the effect of anti-$\alpha_v$, blocking the $\beta_3$ integrin subunit had no effect on the survival of dopaminergic neurones with either a high (FIG. 9b) or low (FIG. 9c) concentration of MPP+.

The results from these experiments suggest that OPN is neuroprotective. However this effect is not mediated through an interaction between the OPN protein and the $\alpha_v\beta_3$ integrin receptor.

The invention claimed is:

1. A method of treating neurodegeneration in a subject in need thereof, which method comprises the step of administering to the subject a therapeutically effective amount of a polypeptide, wherein the amino acid sequence of the polypeptide consists of the amino acid sequence shown in SEQ ID NO: 9.

2. A method according to claim 1, wherein said neurodegeneration is a loss of dopaminergic neurons.

3. A method according to claim 1, wherein said neurodegeneration is associated with a neurodegenerative disorder.

4. A method according to claim 3, wherein the neurodegenerative disorder is Parkinson's disease.

5. A method according to claim 1, wherein said neurodegeneration is associated with aging.

* * * * *